United States Patent [19]

Wilcox

[11] 4,308,104
[45] Dec. 29, 1981

[54] SELF-CONTAINED DISTILLATION APPARATUS

[76] Inventor: Charles R. Wilcox, Rt. 2, Box 435, Atlanta, Tex. 75551

[21] Appl. No.: 142,080

[22] Filed: Apr. 21, 1980

[51] Int. Cl.³ .............................................. B01D 3/02
[52] U.S. Cl. ................................. 202/185 E; 202/235
[58] Field of Search ............ 202/185 R, 185 E, 185 D, 202/163, 176, 177, 182, 235

[56] References Cited

U.S. PATENT DOCUMENTS 1,437,743  12/1922  Arii .................................. 202/185 D
3,694,321  9/1972  Marovich et al. ............... 202/185 E

*Primary Examiner*—Frank Sever

[57] ABSTRACT

A self-contained alcohol still capable of producing fuel grade alcohol. A series of cooling coils are arranged in an inclined manner inside a cooling water medium to provide condensing and reflux. The first stage coil is attached to a reflux zone above the evaporation chamber. This arrangement permits the vapor to be cooled and liquified as it progresses through the various coils. The cooling water is caused to be heated as it moves from the entrance to exit points. The condensing rate is controlled by the rate cooling water is allowed to pass through the unit. This allows elimination of numerous complicated external controls and provides for desired results from common construction methods and extremely simple operating procedures.

4 Claims, 1 Drawing Figure

SELF-CONTAINED DISTILLATION APPARATUS

BRIEF SUMMARY OF THE INVENTION

This invention is a self-contained Distillation Apparatus. Its primary purpose is to extract fuel grade alcohol from a weaker alcohol-water solution; however, it is suitable for the evaporation and condensation of many liquids.

BRIEF DESCRIPTION OF THE DRAWINGS

The Figure is a side view of the apparatus.

DETAILED DESCRIPTION

Figure 1:
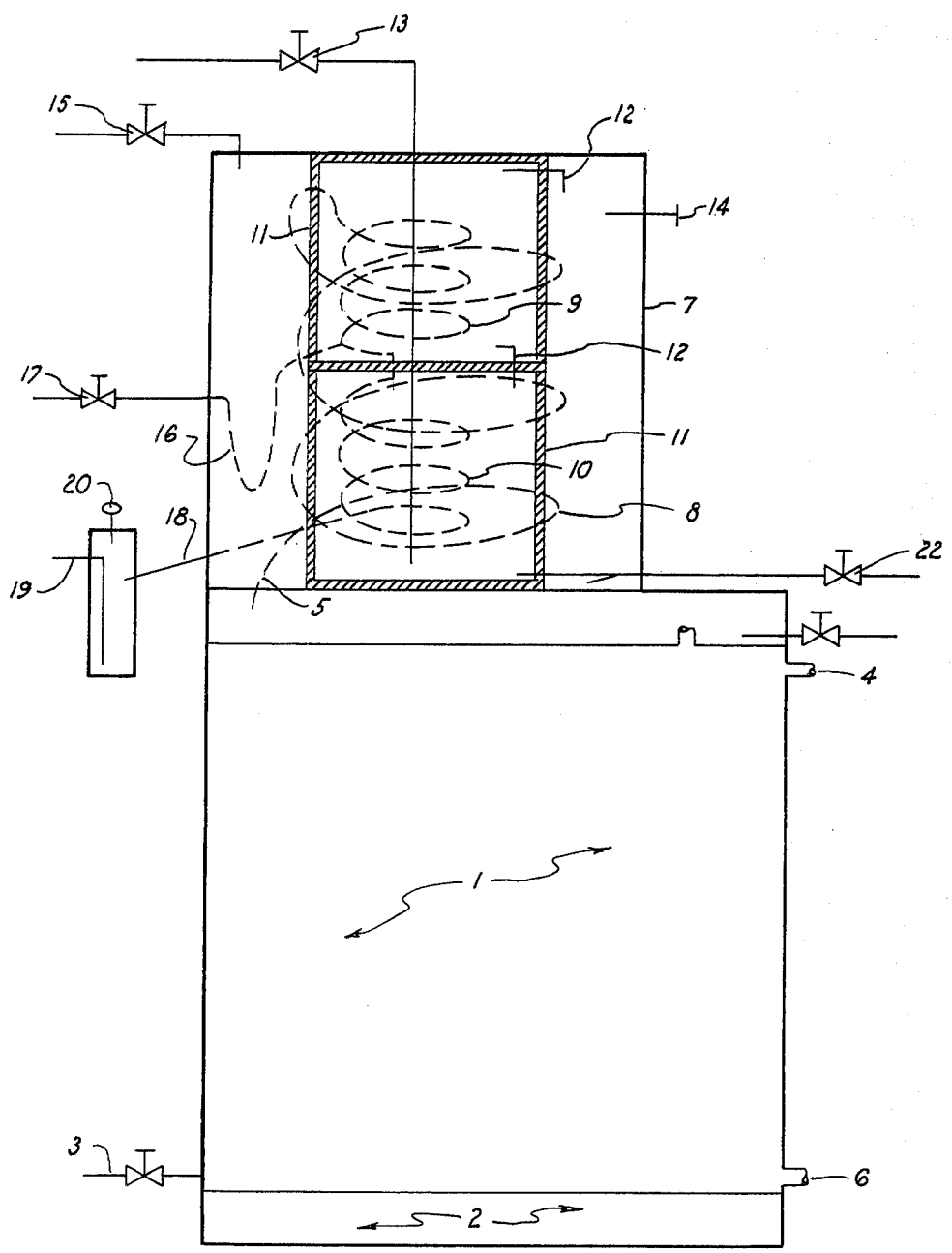

There is an evaporation chamber 1 that contains a heat source 2 such as a gas burner, wood/coal fire box or a steam coil. The evaporation chamber has a drain valve 3 and a fill opening 4 which is closed by a pressure cap after the chamber is filled to the desired level with the solution to be distilled. The chamber has a connecting link to the condensing unit 5. The evaporation chamber also has a flush connection 6 for cleaning. The condensing unit 7 is an enclosed container made of durable material such as steel. The condensing unit has a primary cooling coil 8 and a second stage cooling coil 9 made of tubing such as copper or aluminum. There may be additional stage coils 10 as required to obtain the desired purity of alcohol. The cooling water in contact with the various stage coils is separated and insulated by a membrane 11. A tube 12 is provided to allow the cooling water to pass from one cooling stage to the next. The condensing unit 7 has a fresh water supply tube 13 that directs cooling water from the tap or any other suitable source to the bottom of the final stage cooling coil area. The condensing unit 7 has a temperature gauge 14 to assist in regulating the unit. The condensing unit 7 has a cooling water discharge valve 15 to regulate the temperature of the cooling water to produce the desired concentration of alcohol. The second stage coil 9 has a connection through a bent tube 16 forming a liquid trap and a valve 17 and is routed to any collection container. The final stage coil dumps into a gas chamber 18 where methane gas is collected. The methane gas chamber has a submerged alcohol discharge line 19 that dispenses concentrated alcohol liquid under very low pressure into any collection container. The gas chamber also has a pressure relief valve 20 for additional safety. Methane gas is collected and routed through a line 21 and a regulator 22 to a burner in the fire box 2 or through a compressor to a storage vessel. A dividing partition 23 is included in the upper portion of the evaporation chamber forming a condensate table. This partition has a raised overflow 24 to retain condensate liquid on the table. It also has a drain valve 25 to purge the table when necessary.

I claim:

1. An alcohol still, comprising
   an evaporator zone;
   a condenser zone positioned above said evaporator zone;
   a single reflux container means of predetermined horizontal cross-sectional area positioned between said evaporator and condenser zones.
   vapor conduit means extending from said evaporator means through and into said reflux container means, a vertical predetermined dimension;
   condenser conduit means extending from said reflux container means a predetermined upwardly inclined distance into said condenser zone;
   said area, dimension and distance only, cooperating to provide sufficient reflux for said apparatus during operation therof.

2. The alcohol still of claim 1 wherein said condenser conduit means extends through a plurality of stages within the condenser zone, each stage providing a degree of isolation of the vapor means and cooling water means between stages;
   wherein cooling water means enters the condenser means at the final condenser stage; cooling water conduit means progresses through the condensing stages in descending order and finally discharges from the first stage of the condenser means.

3. The alcohol still in claim 1 wherein said condenser conduit means has an intermediate liquid discharge means extending from the condenser conduit means between stages to a collection container;
   said intermediate liquid discharge means is shaped to form a liquid trap, preventing the release of vapor;
   said condenser means has a liquid discharge means at the final stage.

4. The alcohol still in claim 1 wherein condensing water supply is equipped with a flow rate control device; a cooling water conduit means is provided between stages.

* * * * *